March 12, 1974 H. HOLTKAMP Plant Pat. 3,514
AFRICAN VIOLET
Filed Aug. 24, 1972
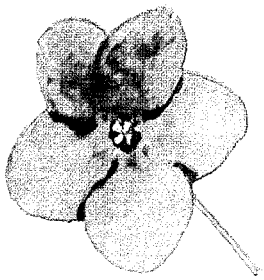
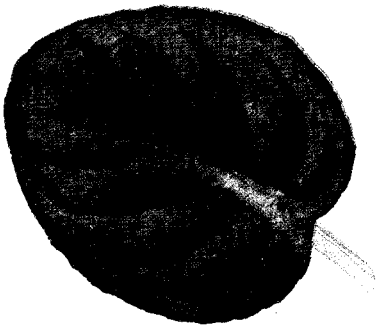
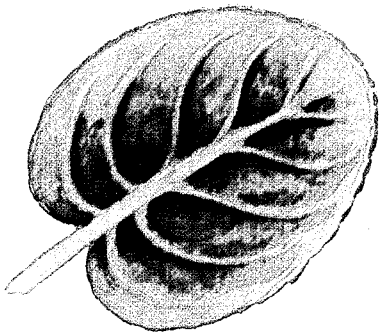
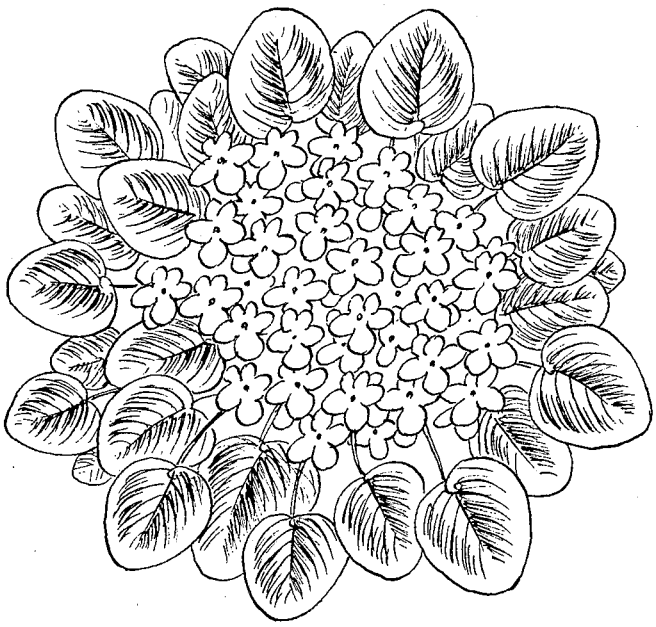

United States Patent Office

Plant Pat. 3,514
Patented Mar. 12, 1974

3,514

AFRICAN VIOLET

Hermann Holtkamp, Werther Strasse 5-7, Postfach 19, 4243 Isselburg, Germany

Filed Aug. 24, 1972, Ser. No. 283,495
Int. Cl. A01h *5/00*
U.S. Cl. Plt.—69 1 Claim

ABSTRACT OF THE DISCLOSURE

A hybrid violet of a descendant of a cross between *Saintpaulia ionantha* and *Saintpaulia shumensis* species which has permanent characteristics including strength of stem, fast and vigorous growth, profuse flowering, uniform bouquet, prolonged blooming period, resistance to disease, reliability in initiating new plantlets, retention of flowers past maturity on their respective stems, and uniformity throughout the life cycle.

BRIEF SUMMARY

The present new variety was originated by me by crossing an unpatented African violet variety, "Rhapsodie Bordeaux Red," Type 14/2, with another unpatented African Violet "Rhapsodie Red," Type 11/145. Both of these varieties were developed by me as the result of an extensive breeding program, and the plants had substantially the same general physical characteristics as "Rhapsodie Gisela," disclosed in my United States Letters Patent PP 3,053 of Apr. 20, 1971, apart from color, and the smaller size of individual flowers and plants.

In the present variety the individual flowers are relatively small and red with three larger petals a lighter shade than two smaller ones. The plants themselves have generally the same physical characteristics as the plants disclosed in the above-designated patent, in their strength of stem, profuse flowering, uniform bouquet, prolonged blooming period, resistance to disease, reliability and uniformity. The color and size of the individual flowers are the principal features that distinguish this variety from those of the variety shown in said patent, and in other varieties of "Rhapsodie."

DESCRIPTION OF DRAWINGS

The upper illustrations show, in full color, one of the flowers, and the opposite sides of one of the leaves; and below, in pen and ink, a top plan view in reduced size of a plant showing a flower head and a wreath of leaves therearound.

DETAILED DESCRIPTION

Name: "Rhopsodie" Carmen
Male Parent: "Rhapsodie" Bordeaux Red, Type 14/2
Female Parent: "Rhapsodie" Red, Type 11/145
Plants: 3 to 4 inches tall Leaves: Borne in rosette arrangement from 6 to 8 inches in diameter
- *Shape.*—Oval
- *Length.*—3 to 3½ inches
- *Width.*—2½ to 3 inches
- *Upper side.*—Heavily hairy
- *Underside.*—Medium hairy
- *Color.*—Upper side dark green. Underside reddish Petiole: Round
Flowers: Upright, central flower head
Individual flowers: Quinquepartite, bilaterally symmetrical
- *Size.*—1 to 1½ inches in diameter
- *Color.*—Red, with three larger petals of lighter shade
- *Calyx.*—Quinquepartite
- *Peduncles.*—Multiflorous, 6 to 8 flowers Genital organs:
- *Stamens.*—Two fructified
- *Anthers.*—Golden yellow
- *Ovary.*—Pilous
- *Seed capsule.*—Does not push through
- *Roots.*—Well developed root system, white when young and active, turning brownish on older plants The color designations, according to "Dictionary of Color" by Maerz and Paul are as follows:

| | Plate Letter | No. |
|---|---|---|
| Body of leaf: | | |
| Upper side medium green | 21 I | 7 |
| Under side | 45 J | 7 |
| Petiole | 44 C | 1 |
| Main body of flowers: | | |
| Three large petals | 51 E | 6 |
| Two small petals | 52 H | 11 |
| Anthers | 9 L | 3 |

GENERAL CHARACTERISTICS

There may be minor variations in the leaf size, shape and color and in the shape of the flowers, which variations are common to African violets, but there is substantial uniformity in the other characteristics hereinabove described that distinguish it from the other varieties, including the central, upright flower head within and above a wreath of leaves of rosette arrangement relative to the flower head, and relatively small individual flowers of red hue in which the two smaller petals are of darker shade than the three larger petals.

I claim:

1. A distinct variety of African violet substantially as herein shown and described, characterized by a habit of bearing a large, central, upright flower head within a wreath of green leaves extending around said flower head, and the individual flowers of which are from approximately 1 to 1½ inches in diameter in which the five petals are red with the two smaller petals of the five being a deeper red than the three larger ones.

No references cited.

ROBERT E. BAGWILL, Primary Examiner